United States Patent [19]

Kobzina

[11] 3,956,315

[45] May 11, 1976

[54] HERBICIDAL N-(3-CYANO-4-ALKYLTHIEN-2-YL) UREAS

[75] Inventor: John W. Kobzina, Walnut Creek, Calif.

[73] Assignee: Chevron Research Company, San Francisco, Calif.

[22] Filed: Mar. 21, 1974

[21] Appl. No.: 453,231

[52] U.S. Cl. ............................ 260/332.2 A; 71/90
[51] Int. Cl.² ..................................... C07D 333/24
[58] Field of Search ................ 260/332.2 A, 553 R

[56] References Cited
UNITED STATES PATENTS 3,326,663   6/1967   Soloway et al. .................... 71/2.6

FOREIGN PATENTS OR APPLICATIONS 2,084,629   12/1971   France ............................ 260/332.2
2,040,579   2/1971   Germany ......................... 260/332.2

*Primary Examiner*—James O. Thomas, Jr.
*Assistant Examiner*—A. Siegel
*Attorney, Agent, or Firm*—G. F. Magdeburger; John Stoner, Jr.; Raymond Owyang

[57] ABSTRACT

Novel N-(3-cyano-4-alkylthien-2-yl) ureas are selective pre- and/or post-emergent herbicides.

3 Claims, No Drawings

HERBICIDAL N-(3-CYANO-4-ALKYLTHIEN-2-YL) UREAS

DESCRIPTION OF THE PRIOR ART

Thienyl-substituted ureas are disclosed in German Offen. No. 2,040,579, published Feb. 25, 1971; French Pat. No. 2,084,629, issued Jan. 29, 1972; and German Offen. No. 2,122,636, published Dec. 2, 1971.

DESCRIPTION OF THE INVENTION

The thienyl ureas of the invention may be represented by the following formula (I):

(I) 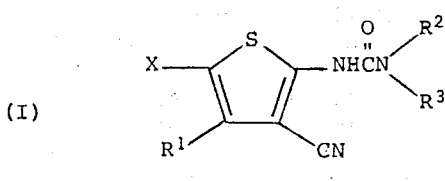

wherein X is hydrogen, fluoro, chloro or bromo; $R^1$ is alkyl of 1 to 10 carbon atoms, cycloalkyl of 3 to 7 carbon atoms, or phenyl substituted with up to 2 (0 to 2) fluoro, chloro or bromo; $R^2$ is hydrogen or alkyl of 1 to 6 carbon atoms and $R^3$ is hydrogen or alkyl of 1 to 6 carbon atoms.

Representative alkyl groups which $R^1$, $R^2$ and $R^3$ may represent are methyl, ethyl, n-propyl, isopropyl and butyl. Representative cycloalkyl groups which $R^1$ may represent are cyclopropyl, cyclobutyl, cyclopentyl, cyclohexyl and cycloheptyl. Representative halophenyl groups which $R^1$ may represent are 2-fluorophenyl, 4-fluorophenyl, 4-chlorophenyl, 3,4-dichlorophenyl and 3-bromophenyl.

The preferred X group is hydrogen or chloro. The most preferred X group is hydrogen. The preferred $R^1$ group is alkyl of 3 to 6 carbon atoms, cycloalkyl of 3 to 6 carbon atoms, or phenyl. The most preferred $R^1$ group is alkyl of 3 to 6 carbon atoms. The preferred $R^2$ group is hydrogen. The preferred $R^3$ group is alkyl of 1 to 6 carbon atoms, more preferably of 1 to 3 carbon atoms.

The preferred thienyl ureas of formula (I) are therefore those wherein X is hydrogen or chloro, $R^1$ is alkyl of 3 to 6 carbon atoms, cycloalkyl of 3 to 6 carbon atoms or phenyl; $R^2$ is hydrogen, and $R^3$ is alkyl of 1 to 6 carbon atoms, and the most preferred thienyl ureas of formula (I) are those wherein X is hydrogen, $R^1$ is alkyl of 3 to 6 carbon atoms, $R^2$ is hydrogen and $R^3$ is alkyl of 1 to 3 carbon atoms.

Illustrative thienyl ureas of formula (I) are:
N-(3-cyano-4-methylthien-2-yl) urea,
N-(3-cyano-4-ethyl-5-chlorothien-2-yl) urea,
N-(3-cyano-4-isopropyl-5-bromothien-2-yl) urea,
N-(3-cyano-4-n-propylthien-2-yl)-N'-methyl urea,
N-(3-cyano-4-t-butylthien-2-yl)-N'-methyl urea,
N-(3-cyano-4-sec-butyl-5-bromothien-2-yl)-N'-methyl urea,
N-(3-cyano-4-cyclopentyl-5-chlorothien-2-yl)-N'-methyl urea,
N-(3-cyano-4-o-bromophenyl-5-chlorothien-2-yl)-N'-hexyl urea,
N-(3-cyano-4-isopropylthien-2-yl)-N',N'-dimethyl urea,
N-(3-cyano-4-cyclopropyl-5-chlorothien-2-yl)-N',N'-diethyl urea,
N-(3-cyano-4-o-fluorophenylthien-2-yl)-N',N'-dimethyl urea, and
N-(3-cyano-4-o,p-dichlorophenylthien-2-yl)-N',N'-dimethyl urea.

The thienyl ureas of formula (I) are prepared by reacting a 2-aminothiophene (II), phosgene (III) and an amine (IV) according to the following reaction:

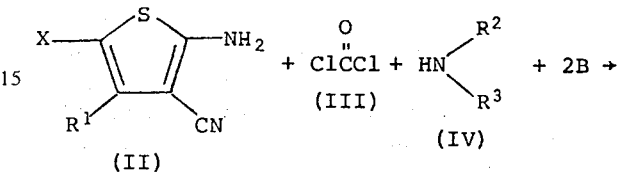

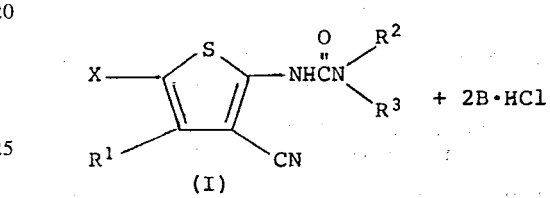

wherein X, $R^1$, $R^2$ and $R^3$ have the same significance as previously defined and B is an acid acceptor.

The above reaction is conducted by more or less conventional procedures. For example, the aminothiophene can be reacted with phosgene, and the resulting carbamoyl chloride product can be reacted with the amine (IV) to produce the product (I). Alternatively, the entire amounts of reactants (II), III) and (IV) can be reacted together. Generally, substantially equimolar amounts of reactants (II), (III) and (IV) are employed, although an excess of phosgene or the amine (IV) also can be employed. Generally, at least 2 to 3 mols of acid acceptor is employed per mol of phosgene. Suitable acid acceptors are trialkylamines, such as triethylamines, or a pyridine compound, such as pyridine or α-picoline. Reaction temperatures generally vary from 0°C. to 50°C. The product (I) is isolated by conventional procedures such as extraction, distillation, chromatography and crystallization.

The thienyl ureas of formula (I) wherein $R^2$ is hydrogen and $R^3$ is alkyl can also be prepared by reacting the 2-aminothiophene (II) and an alkyl isocyanate (III) according to the following reaction:

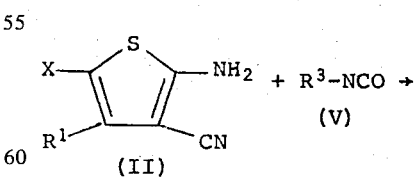

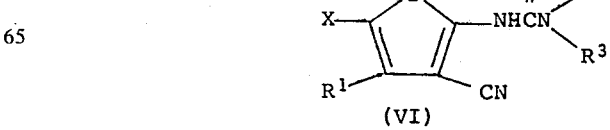

wherein X, $R^1$ and $R^3$ have the same significance as previously defined.

This second reaction is conducted by the conventional procedures generally employed for the reaction of amines and isocyanates. Thus, this reaction is generally conducted with substantially equimolar amounts of the reactants (II) and (V) or with an excess of the isocyanate (V), preferably in the presence of an inert solvent such as dimethoxyethane or dimethylformamide, and optionally in the presence of a small amount of a basic catalyst such as a tertiary trialkylamine, e.g., triethylamine, or dialkyl tin dialkanoates, e.g., dibutyl tin dilaurate. Suitable reaction temperatures vary from about 0°C. to 150°C., preferably from about 50°C. to 125°C. The product (VI) is isolated and purified by conventional procedures such as distillation, crystallization and chromatography.

EXAMPLES

The preparation of the thienyl ureas of the invention is illustrated by the following examples.

Example 1 — Preparation of
N-(3-cyano-4-sec-butylthien-2-yl)-N'-methyl urea

2-Amino-3-cyano-4-sec-butylthiophene was prepared from sulfur and 1,1-dicyano-2-methyl-2-sec-butylethylene by the procedure described in *Chem. Ber.* 99, 2712 (1966).

A solution of 5 g 2-amino-3-cyano-4-sec-butylthiophene and 10 ml methyl isocyanate in 20 ml dimethoxyethane was stirred at about 25°C. for 2 days and then at reflux for 6 hours. The reaction mixture was evaporated under reduced pressure and the residue was chromatographed on a silica-gel column. The product, a white solid melting at 149°–152°C., was eluted with 70% ether-30% hexane. The infrared spectrum of the product showed cyano absorption at 4.5 microns. Sulfur analysis for the product is tabulated in Table I.

Example 2 — Preparation of
N-(3-cyano-4-cyclopropylthien-2-yl)-N'-methyl urea

2-Amino-3-cyano-4-cyclopropylthiophene was prepared from sulfur and 1,1-dicyano-2-methyl-2-cyclopropylethylene in diethylamine by the procedure described in *Chem. Ber.* 99, 2171 (1966).

A solution of 10 g 2-amino-3-cyano-4-cyclopropylthiophene, 6.94 g methyl isocyanate and 0.1 g dibutyl tin dilaurate in 20 ml dimethoxyethane was refluxed for 7 hours and then allowed to stand at about 25°C. overnight. The reaction mixture was evaporated and the resulting residue was chromatographed on silica gel. The product, a pale-green solid melting at 169°–172°C., was eluted with 1:1 ether-hexane. Sulfur analysis for the product is tabulated in Table I.

Example 3 — Preparation of
N-(3-cyano-4-t-butylthien-2-yl)-N'-methyl urea

A solution of 4 g 2-amino-3-cyano-4-t-butylthiophene, 1.27 g methyl isocyanate and 3 ml triethylamine in 20 ml dimethylformamide was heated at 130°C. for 3 hours and then allowed to stand at about 25°C. overnight. The dimethylformamide was removed by distillation and the residue was crystallized from ether to give the product, as a tan solid, m.p. 212°–214°C. The infrared spectrum of the product showed cyano absorption at 4.6 microns. Sulfur analysis for the product is tabulated in Table I.

Example 4 — Preparation of
N-(3-cyano-4-t-butyl-5-chlorothien-2-yl)-N'-methyl urea Gaseous hydrogen chloride was bubbled into a cooled (0°C.) solution of 5 g of 2-amino-3-cyano-4-5-butylthiophene in 20 ml chloroform for 5 minutes. To the resulting mixture was then added dropwise 3.81 g sulfuryl chloride over a 10-minute period. After stirring at 0°C. for 2 hours, the reaction mixture was placed under reduced pressure (water aspirator) at 0°C. to remove gaseous by-products. The reaction mixture was then diluted with 10 ml of a 25% (weight) aqueous sodium hydroxide solution and 5 ml of methylene chloride. The organic layer was separated, dried over magnesium sulfate and evaporated under reduced pressure to give an oil residue. The oil was chromatographed on silica gel (1:1 ether-hexane elution) to give 3.7 g of 3-cyano-4-t-butyl-5-chlorothiophene, as a semi-solid. Elemental analysis showed: %S, calc. 14.93, found 15.0; %Cl, calc. 16.5, found 15.8.

A solution of 6.4 g 3-cyano-4-t-butyl-5-chlorothiophene, prepared as described above, 1.71 g methyl isocyanate and 20 drops triethylamine in 20 ml dimethylformamide was heated at 120°–125°C. for 3 hours. The reaction mixture was diluted with 250 ml ice water and extracted with chloroform. The chloroform extracts were dried over magnesium sulfate and evaporated to give an oil. The oil was chromatographed on silica gel (1:1 ether-hexane eluant) to give the product as a brown solid, m.p. 215°–217°C. Sulfur analysis for the product is tabulated in Table I.

Example 5 — Preparation of
N-(3-cyano-4-t-butylthien-2-yl)-N',N'-dimethyl urea

A solution of 3.04 g phosgene in about 25 ml benzene was added to a cooled (0°C.) solution of 5 g 2-amino-3-cyano-4-t-butylthiophene, 5 g diethylamine and 8.4 g triethylamine in 100 ml benzene. The reaction mixture was warmed to about 25°C. and maintained at this temperature for about 16 hours. The reaction mixture was filtered and the filtrate was evaporated to give a black oil. The oil was chromatographed on silica gel. The product, a brown solid melting at 120°–125°C., was eluted from the silica gel with 1:1 ether-hexane. The infrared spectrum of the product showed strong cyano absorption at 4.6 microns and strong carbonyl absorption at 6.0 microns. Sulfur analysis for the product is tabulated in Table I.

UTILITY

The compounds of the present invention are, in general, herbicidal in both pre- and post-emergent applications. For pre-emergent control of undesirable vegetation, the herbicidal compounds will be applied in herbicidally effective amounts to the environment or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaf weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour, or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally, for both pre- and post-emergent control, the herbicidal compounds of the invention are applied at rates of 0.2 to 60 kg/ha., and the preferred rate is in the range 0.5 to 40 kg/ha.

Pre- and post-emergent herbicidal tests on representative compounds of the invention were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 $\mu$/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill.

Post-Emergence Test

The test compound was formulated in the same manner as described above for the pre-emergence test. The concentration of the test compound in this formulation was 5000 ppm. This formulation was uniformly sprayed on 2 similar pots of 24-day-old plants (approximately 15 to 25 plants per pot) at a dose of 33 $\mu$/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

TABLE I

| No. | Compound | Melting Point °C. | Sulfur Analysis Calc. | Found |
|---|---|---|---|---|
| 1 | N-(3-cyano-4-sec-butylthien-2-yl)-N'-methyl urea | 149–152 | 13.51 | 13.7 |
| 2 | N-(3-cyano-4-cyclopropylthien-2-yl)-N'-methyl urea | 169–172 | 14.49 | 13.6 |
| 3 | N-(3-cyano-4-sec-butylthien-2-yl)-N'-methyl urea | 212–214 | 13.51 | 12.92 |
| 4 | N-(3-cyano-4-t-butyl-5-chlorothien-2-yl)-N'-methyl urea | 215–217 | 11.80 | 11.40 |
| 5 | N-(3-cyano-4-t-butylthien-2-yl)-N',N'-dimethyl urea | 120–125 | 12.75 | 12.68 |
| 6 | N-(3-cyano-4-isopropylthien-2-yl)-N'-methyl urea | 177–178 | 14.36 | 14.28 |
| 7 | N-(3-cyano-4-t-butylthien-2-yl)-N'-propyl urea | 154–158 | 12.08 | 12.07 |
| 8 | N-(3-cyano-4-isopropylthien-2-yl)-N',N'-dimethyl urea | 113–116 | 17.7 N | 17.8 |
| 9 | N-(3-cyano-4-phenylthien-2-yl)-N'-methyl urea | 190–194 | 12.46 | 11.8 |
| 10 | N-(3-cyano-4-cyclopropylthien-2-yl)-N',N'-dimethyl urea | 171–172 | 13.63 | 13.6 |
| 11 | N-(3-cyano-4-isopropylthien-2-yl) urea | 190–192 | 15.32 | 18.7 |
| 12 | N-(3-cyano-4-sec-butylthien-2-yl)-N'-ethyl urea | 104–106 | 12.76 | 13.2 |
| 13 | N-(3-cyano-4-cyclopropylthien-2-yl)-N'-ethyl urea | 174–180 | 13.63 | 13.0 |
| 14 | N-(3-cyano-4-cyclopropylthien-2-yl)-N'-t-butyl urea | 227–230 | 12.18 | 12.1 |
| 15 | N-(3-cyano-4-cyclohexylthien-2-yl)-N'-methyl urea | 225–226 | 12.17 | 12.1 |

TABLE II

| Compound No. | Herbicidal Effectiveness Pre/Post | | | | | |
|---|---|---|---|---|---|---|
| | O | W | C | M | P | L |
| 1 | 0/80 | 15/85 | 30/95 | 100/100 | 75/100 | 75/100 |
| 2 | 0/45 | 0/45 | 0/85 | 80/100 | 55/100 | 60/100 |
| 3 | 25/75 | 60/75 | 50/60 | 100/100 | 0/90 | 95/100 |

TABLE II-continued

| Compound No. | Herbicidal Effectiveness Pre/Post | | | | | |
|---|---|---|---|---|---|---|
| | O | W | C | M | P | L |
| 4 | 0/25 | 0/20 | —/10 | 90/100 | 70/95 | 100/100 |
| 5 | 0/90 | 0/90 | 0/85 | 0/100 | 0/95 | 0/100 |
| 6 | 15/94 | 95/89 | 100/95 | 100/100 | 65/100 | 95/100 |
| 7 | 0/0 | 0/0 | 0/0 | 95/100 | 0/35 | 95/100 |
| 8 | 13/— | 27/— | 27/— | 93/— | 73/— | 99/— |
| 9 | 10/20 | 0/20 | —/10 | 80/95 | 80/90 | 80/90 |
| 10 | 0/15 | 0/15 | 0/15 | 0/25 | 0/25 | 0/25 |
| 11 | 20/0 | 10/0 | 0/0 | 70/0 | 0/0 | 70/0 |
| 12 | 0.45 | 0/35 | 0/10 | 100/100 | 15/40 | 100/100 |
| 13 | 0/0 | 0/35 | 0/0 | 100/90 | 95/40 | 100/78 |
| 14 | 0/0 | 0/0 | 15/0 | 0/35 | 0/20 | 100/0 |
| 15 | 0/25 | 0/60 | 0/25 | 95/95 | 70/65 | 100/100 |

O = Wild Oats (Avenua fatua)
M = Mustard (Brassica arvensis)
W = Watergrass (Echinochloa crusgalli)
P = Pigweed (Amaranthus retroflexus)
C = Crabgrass (Digitaria sanguinalis)
L = Lambsquarter (Chenopodium album)

What is claimed is:
1. A compound of the formula

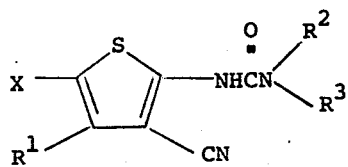

wherein X is hydrogen; $R^1$ is alkyl of 3 to 6 carbon atoms; $R^2$ is hydrogen; and $R^3$ is alkyl of 1 to 6 carbon atoms.

2. N-(3-cyano-4-isopropylthien-2-yl)-N'-methyl urea, according to claim 1.

3. N-(3-cyano-4-sec-butylthien-2-yl)-N'-methyl urea, according to claim 1.

* * * * *